United States Patent
Smigelski, Jr. et al.

(10) Patent No.: US 6,576,801 B2
(45) Date of Patent: *Jun. 10, 2003

(54) PROCESS FOR THE NEUTRALIZATION OF RESIDUAL ACID SPECIES IN CRUDE DIHYDRIC PHENOLS

(75) Inventors: Paul Michael Smigelski, Jr., Schenectady, NY (US); Timothy Brydon Burnell, Schenectady, NY (US); Patrick Joseph McCloskey, Watervliet, NY (US)

(73) Assignee: General Electric Company, Schenectady, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/683,866

(22) Filed: Feb. 25, 2002

(65) Prior Publication Data

US 2002/0143134 A1 Oct. 3, 2002

Related U.S. Application Data

(63) Continuation of application No. 09/798,221, filed on Mar. 2, 2001, now Pat. No. 6,414,106.

(51) Int. Cl.$^7$ .......................... C07C 37/68; C08G 64/00
(52) U.S. Cl. ...................... 568/724; 568/749; 568/750; 528/196; 528/198
(58) Field of Search ................. 528/196, 198; 568/717, 722, 724, 716, 723, 749, 750

(56) References Cited

U.S. PATENT DOCUMENTS

| 5,783,733 A | 7/1998 | Kissinger |
| 5,880,248 A | 3/1999 | Sakashita et al. |
| 6,288,973 B1 | 6/2001 | McCloskey et al. |

FOREIGN PATENT DOCUMENTS

| EP | 0 552 518 B1 | 7/1993 |
| JP | 8 337546 A | 12/1996 |
| WO | WO 02/070445 A1 | 2/2002 |

OTHER PUBLICATIONS

Kirk–Othmer Encyclopedia of Chemical Technology, Third Edition, vol. 18, pp. 479–488, (1982).
Kirk–Othmer Encyclopedia of Chemical Technology, Fourth Edition, vol. 19, pp. 584–608, (1996).
Derwent Publication Abstract XP00220389 (Dec. 12, 1995).
International Search Report mailed Jul. 9, 2002.

*Primary Examiner*—Johann Richter
*Assistant Examiner*—Elvis O. Price

(57) ABSTRACT

The present invention relates to a method of neutralizing residual acid species in crude dihydric phenol comprising the step of introducing a thermally stable organic base selected from the group consisting of tetraalkyl phosphonium hydroxides, tetraorganophosphonium carboxylic acid salts, or a mixture thereof into the crude dihydric phenol.

19 Claims, No Drawings

PROCESS FOR THE NEUTRALIZATION OF RESIDUAL ACID SPECIES IN CRUDE DIHYDRIC PHENOLS

Cross Reference to Related Applications

This is a continuation of U.S. patent application Ser. No. 09/798,221 filed on Mar. 2, 2001, which is incorporated by reference herein now U.S. Pat. No. 6,404,106.

BACKGROUND OF INVENTION

Dihydric phenols are useful in the commercial manufacture of various polymers including polyarylates, polyamides, epoxies, polyetherimides, polysulfones and polycarbonates. The acid catalyzed reaction of phenol with aldehydes or ketones is a well known method to prepare the 4,4'-dihydric phenol. In particular, when phenol is reacted with acetone, the dihydric phenol 2,2-bis(4-hydroxy-phenyl) propane, also known as bisphenol-A or BPA is formed. BPA may be used to prepare polycarbonates, polyarylates, and copolyestercarbonates, as well as epoxies.

The manufacture of dihydric phenols, such as BPA, requires the use of an acid catalyst. Residual acid from the crude, isolated dihydric phenol will cause subsequent cracking of the dihydric phenol during isolation and purification. In the case of BPA, for instance, the cracking process may lead to the formation of isopropenyl phenol, an unwanted side product. Further, residual acid remaining in the final dihydric phenol product can cause catalyst quenching if the dihydric phenol is used in the manufacture of polycarbonate by the melt process.

Typically, a low level of base, such as sodium hydroxide, is added to the crude dihydric phenol prior to purification to reduce the level of cracking during purification. The residual base will remain in the final dihydric phenol product, and in the final polymer product, if the dihydric phenol is used in a melt process. In particular, alkali metals in polycarbonate prepared by the melt process result in the undesirable formation of side branching reactions.

It would be desirable to reduce the level of cracking during the purification of a dihydric phenol. Further, it would be desirable to reduce cracking without the introduction of materials that result in the formation of side branching products in a polymer prepared from the dihydric phenols.

SUMMARY OF INVENTION

The present invention relates to a method of neutralizing residual acid species in crude dihydric phenol comprising the step of introducing a thermally stable organic base selected from the group consisting of tetraalkyl phosphonium hydroxides, tetraorganophosphonium carboxylic acid salts, or a mixture thereof into the crude dihydric phenol.

The above described and other features are exemplified by the following figures and detailed description.

DETAILED DESCRIPTION

The present invention may be understood more readily by reference to the following detailed description of preferred embodiments of the invention and the examples included therein.

Before the present compositions of matter and methods are disclosed and described, it is to be understood that this invention is not limited to specific synthetic methods or to particular formulations, as such may, of course, vary. It is also to be understood that the terminology used herein is for the purpose of describing particular embodiments only and is not intended to be limiting.

In the following specification, reference will be made to a number of terms that shall be defined to have the following meanings.

The singular forms "a", "an" and "the" include plural referents unless the context clearly dictates otherwise.

"Optional" or "optionally" means that the subsequently described event or circumstance may or may not occur, and that the description includes instances where the event occurs and instances where it does not.

As used herein, the term "melt polycarbonate" refers to a polycarbonate made by the transesterification of a carbonate diester with a dihydroxy compound.

"BPA" is herein defined as bisphenol A or 2,2-bis(4-hydroxyphenyl)propane.

The terms "diphenol" and "dihydric phenol" as used herein are synonymous.

A known method for the preparation of bisphenols requires the condensation of ketones and phenol in the presence of a sulfonic acid based polystyrene ion exchange resin (IER), as described, for example in U.S. Pat. No. 5,783,733. The crude bisphenol product from these processes typically contain low levels of sulfonic acid polystyrene oligomers. The presence of these oligomers during subsequent heat treatment, for example desorption of phenol and/or melt crystallization, can result in cracking of bisphenol. In the case of BPA, cracking of the bisphenol produces isopropenyl phenol, an unwanted side product.

Typical IER used as catalysts in the production of dihydric phenols include cationic exchange resins, in particular strong-acid types of resins. Examples include, but are not limited to sulfonated copolymers of styrene and a cross-linking agent, e.g., a difunctional monomer such as divinylbenzene.

In order to reduce cracking, it is known to neutralize the sulfonic acid oligomers in the crude dihydric phenol prior to purification. Typically, a base, such as sodium hydroxide, is added to neutralize the sulfonic acids prior to purification. During isolation and purification of the dihydric phenol, however, such as in the case of sodium hydroxide, the sodium sulfonate salts and more basic forms of sodium, such as sodium hydroxide or salt of the dihydric phenol, can remain in the final dihydric phenol product.

If the dihydric phenol is used in a melt polymerization process, it is desirable to minimize the added level of excess base in the preparation and processing of the dihydric phenol, such as sodium hydroxide, to ensure maximum hydrolytic and thermal stability, as well as to minimize color generation in the final polymer. While alkali earth metal bases are the catalysts of choice for the melt polymerization process, the use of alkali earth metal bases, such as sodium hydroxide, also results in the generation of side products that cause branching in the melt resin. These side products include "Fries" products.

As used herein the term "Fries" or "fries" refers to a repeating unit in polycarbonate having the following formula (I):

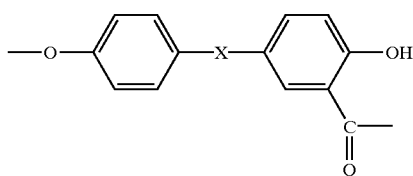

where the X variable represents or

Variable $R_c$ and $R_d$ each independently represent a hydrogen atom or a monovalent hydrocarbon group and may form a ring structure. Variable $R_e$ is a divalent hydrocarbon group.

It is very desirable to have a low Fries content in the polycarbonate product, as Fries products reduce the performance characteristics of the polycarbonate, such as the ductility. Higher Fries contents results in lower ductility. Preparing polycarbonate by the melt process results in the formation of Fries products.

Minimizing or eliminating the alkali earth metal, such as sodium, in the process of preparing the dihydric phenols will minimize the branching side product formation in the melt process to prepare polymer from the dihydric phenols. In particular, reduction of residual alkali earth metal base in the bisphenol used to prepare polycarbonate is desirable. Excess residual acid in the dihydric phenol, however, that has not been neutralized, will negatively impact the polymerization rate as it will neutralize the alkali earth metal used as the catalyst in the melt polymerization.

In the present invention, it was unexpectedly found that the addition of a thermally stable organic base, preferably stable at temperatures above 200° C., selected from the group consisting of tetraalkyl phosphonium hydroxides, tetraorganophosphonium carboxylic acid salts, or a mixture thereof, to the crude dihydric phenol, effectively neutralizes the residual acid species, such as aryl sulfonic acid species, while producing a negligible amount of the branching side products, such as Fries product, in the final polymer prepared from the dihydric phenol. Preferably, the branching side products are present in the final polymer at less than 100 ppm, based on the polymer. The thermally stable organic bases, are strong enough bases to effectively neutralize the residual aryl sulfonic acid species introduced by the IER throughout the course of the melt polymerization.

The thermally stable organic base is preferably introduced into crude dihydric phenol in an amount of from about 1 to about 25 molar equivalents of thermally stable organic base per mole of sulfonic acid compound to provide effective neutralization; more preferably from about 1 to about 15 molar equivalents of thermally stable organic base per mole of sulfonic acid compound. In production, it is expected that from about $1.0 \times 10^{-8}$ to about $5.0 \times 10^{-6}$ moles of sulfonic acid groups per mole of dihydric phenol are present in the crude dihydric phenol. The thermally stable organic base may be added to the crude dihydric phenol as a solid, for example a powder, or it may be dissolved in a solvent, for example water or alcohol. By "crude dihydric phenol" it is meant the untreated product from a process using a sulfonic acid based material, for example a process utilizing a sulfonic acid based polystyrene ion exchange resin (IER).

Examples of suitable tetraalkylphosphonium hydroxides include, but are not limited to, tetramethylphosphonium hydroxide, tetraethylphosphonium hydroxide, tetrapropylphosphonium hydroxide, tetrabutylphosphonium hydroxide, tetrapentylphosphonium hydroxide, tetrahexylphosphoniuim hydroxide, tetraheptylphosphonium hydroxide, tetraoctylphosphonium hydroxide, tetradecylphosphonium hydroxide, tetradodecylphosphonium hydroxide, tetratolylphosphonium hydroxide, tetraphenylphosphonium hydroxide, and a mixture thereof.

In one embodiment, the tetraalkylphosphonium hydroxide is tetrabutylphosphonium hydroxide.

Examples of suitable tetraorganophosphonium carboxylic acid salts or derivatives thereof, include, but are not limited to: tetramethylphosphonium acetate, tetraethylphosphonium acetate, tetrapropylphosphonium acetate, tetrabutylphosphonium acetate, tetrapentylphosphonium acetate, tetrahexylphosphonium acetate, tetraheptylphosphonium acetate, tetraoctylphosphonium acetate, tetradecylphosphonium acetate, tetradodecylphosphonium acetate, tetratolylphosphonium acetate, tetraphenylphosphonium acetate, tetramethylphosphonium benzoate, tetraethylphosphonium benzoate, tetrapropylphosphonium benzoate, tetraphenylphosphonium benzoate, tetramethylphosphonium formate, tetraethylphosphonium formate, tetrapropylphosphonium formate, tetraphenylphosphonium formate, tetramethylphosphonium propionate, tetraethylphosphonium propionate, tetrapropylphosphonium propionate, tetramethylphosphonium butyrate, tetraethylphosphonium butyrate, and tetrapropylphosphonium butyrate, and a mixture thereof.

In one embodiment, the tetraorganophosphonium carboxylic acid salt or derivative thereof is tetrabutylphosphonium acetate. As mentioned, dihydric phenols are used in the preparation of polycarbonate by the melt process. The dihydric phenols are transesterified with a carbonic acid diester in the presence of a base catalyst. The dihydric phenols treated according to the method of the present invention are particularly suitable for use in the melt process to prepare polycarbonate, and contribute to improved properties in the final polymer, as the thermally stable organic bases neutralize residual acid species in the dihydric phenol, and introduce only a negligible amount of branching species into the product polymer as compared to the alkali metal bases. The thermally stable organic bases utilized in the present invention for neutralization avoid the problems associated with alkali/alkali earth metal catalysts. For example, the total sodium remaining in a product polymer contributes to worse color and thermal stability and worse hydrolytic stability.

Dihydric phenols which are useful in polycarbonate of may be represented by the general formula

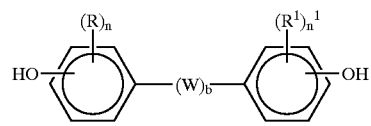

wherein: R is independently selected from halogen, monovalent hydrocarbon, and monovalent hydrocarbonoxy radicals; $R^1$ is independently selected from halogen, monovalent hydrocarbon, and monovalent hydrocarbonoxy radicals: W is selected from divalent hydrocarbon radicals,

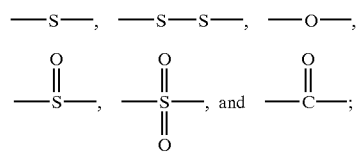

n and $n^1$ are independently selected from integers having a value of from 0 to 4 inclusive; and b is either zero or one.

The monovalent hydrocarbon radicals represented by R and $R^1$ include the alkyl, cycloalkyl, aryl, aralkyl and alkaryl radicals. The preferred alkyl radicals are those containing from 1 to about 12 carbon atoms. The preferred cycloalkyl radicals are those containing from 4 to about 8 ring carbon atoms.

The preferred aryl radicals are those containing from 6 to 12 ring carbon atoms, i.e., phenyl, naphthyl, and biphenyl. The preferred alkaryl and aralkyl radicals are those containing from 7 to about 14 carbon atoms.

The preferred halogen radicals represented by R and $R^1$ are chlorine and bromine.

The divalent hydrocarbon radicals represented by include the alkylene, alkylidene, cycloalkylene and cycloalkylidene radicals. The preferred alkylene radicals are those containing from 2 to about 30 carbon atoms. The preferred alkylidene radicals are those containing from 1 to about 30 carbon atoms. The preferred cycloalkylene and cycloalkylidene radicals are those containing from 6 to about 16 ring carbon atoms.

The monovalent hydrocarbonoxy radicals represented by R and $R^1$ may be represented by the formula —$OR^2$ wherein $R^2$ is a monovalent hydrocarbon radical of the type described hereinafore. Preferred monovalent hydrocarbonoxy radicals are the alkoxy and aryloxy radicals.

Suitable dihydric phenols include, but are not limited to, BPA; 2,2-bis(3,5-dibromo-4-hydroxyphenyl)propane; 2,2-bis(3,5-dimethyl-4-hydroxyphenyl) propane; 1,1-bis(4-hydroxyphenyl)cyclohexane; 1,1-bis(3,5-dimethyl-4-hydroxyphenyl)cyclohexane; 1,1-bis(4-hydroxyphenyl) decane; 1,1-bis(4-hydroxyphenyl)propane; 1,1-bis(4-hydroxyphenyl)cyclodecane; 1,1-bis (3,5-dimethyl-4-hydroxyphenyl)cyclododecane; 4,4-dihydroxyphenyl ether; 4,4-thiodiphenol; 4-4-dihydroxy-3,3-dichlorodiphenyl ether; 4,4-thiodiphenol; 4,4-dihydroxy-3,3-dichlorodiphenyl ether; 4,4-dihydroxy-2,5-dihydroxydiphenyl ether; BPI; 1,1-bis(4-hydroxyphenyl)-1-phenylethane; 1,1-bis(3-methyl-4-hydroxyphenyl)-1-phenylethane, and mixtures thereof. In one embodiment, the residues of dihydric phenol in the polycarbonate comprise 100 mol % of residues derived from BPA.

Optionally, polyfunctional compounds may be utilized. Suitable polyfunctional compounds used in the polymerization of branched polycarbonate include, but are not limited to, 1,1,1-tris(4-hydroxyphenyl)ethane, 4-[4-[1,1-bis(4-hydroxyphenyl)-ethyl]-dimethylbenzyl], trimellitic anhydride, trimellitic acid , or their acid chloride derivatives.

As the diester of carbonic acid, various compounds may be used, including, but not limited to diaryl carbonate compounds, dialkyl carbonate compounds and alkylaryl carbonate compounds. Suitable diesters of carbonic acid include, but are not limited to, diaryl carbonate; bis(4-t-butylphenyl)carbonate; bis(2,4-dichlorophenyl)carbonate; bis(2,4,6-trichlorphenyl)carbonate; bis(2-cyanophenyl) carbonate; bis(o-nitrophenyl) carbonate; ditolyl carbonate; m-cresol carbonate; dinaphthyl carbonate; bis(diaryl) carbonate; diethylcarbonate; dimethyl carbonate; dibutyl carbonate; dicyclohexyl carbonate; and mixtures thereof. Of these, diaryl carbonate is preferred. If two or more of these compound are utilized, it is preferable that one is diaryl carbonate.

Diphenyl carbonates used to make the polyestercarbonates by melt: Suitable carbonate sources, catalysts and reaction conditions are found in U.S. Pat. No. 5,880,248, and Kirk-Othmer Encyclopedia of Chemical Technology, Fourth Edition, Volume 19, pp. 585–600, herein incorporated by reference.

An endcapping agent may optionally be used. Suitable endcapping agents include monovalent aromatic hydroxy compounds, haloformate derivatives of monovalent aromatic hydroxy compounds, monovalent carboxylic acids, halide derivatives of monovalent carboxylic acids, and mixtures thereof.

Suitable endcapping agents include, but are not limited to phenol, p-tert-butylphenol; p-cumylphenol; p-cumylphenolcarbonate; undecanoic acid, lauric acid, stearic acid; phenyl chloroformate, t-butyl phenyl chloroformate, p-cumyl chloroformate, chroman chloroformate, hydrocardanol, nonyl phenol, octyl phenol; nonyl phenyl chloroformate or a mixture thereof. Furthermore, mixed carbonates and esters composed of endcappers from the list above along with phenol or alkylsalicylates are acceptable.

If present, the endcapping agent is preferably present in amounts of about 0.01 to about 0.20 moles, preferably about 0.02 to about 0.15 moles, even more preferably about 0.02 to about 0.10 moles per 1 mole of the dihydric phenol.

Typical catalysts employed in the melt condensation polymerization process include, but are not limited to, alkali metal compounds, alkaline earth metal compounds, quaternary ammonium compounds, quaternary phosphonium compounds and combinations thereof. Other catalysts include, but are not limited to cesium hydrogen phosphate; sodium phosphate; sodium phosphite; cesium sulfate; cesium sodium sulfate; disodium EDTA; sodium sulfite; disodium magnesium EDTA and mixtures thereof.

Useful alkali metal compounds as catalysts include sodium hydroxide, potassium hydroxide, lithium hydroxide, sodium hydrogencarbonate, potassium hydrogencarbonate, lithium hydrogencarbonate, sodium carbonate, potassium carbonate, lithium carbonate, sodium acetate, potassium acetate, lithium acetate, sodium stearate, potassium stearate, lithium stearate, sodium borohydride, lithium borohydride, sodium borophenolate, sodium benzoate, potassium benzoate, lithium benzoate, disodium hydrogenphosphate, dipotassium hydrogenphosphate, dilithium hydrogenphosphate, disodium, dipotassium and dilithium salts of BPA and sodium, potassium, and lithium salts of phenol.

Useful alkaline earth metal compounds as catalysts include calcium hydroxide, barium hydroxide, magnesium hydroxide, strontium hydroxide, calcium hydrogen carbonate, barium hydrogencarbonate, magnesium hydrogencarbonate, strontium hydrogencarbonate, calcium carbonate, barium carbonate, magnesium carbonate, strontium carbonate, calcium acetate, barium acetate, magnesium acetate, strontium acetate, calcium stearate, barium stearate, magnesium stearate, and strontium stearate.

Useful quaternary ammonium compounds as catalysts include tetraalkylammonium compounds such as tetramethylammonium hydroxide and tetraethylammonium hydroxide. Examples of quaternary ammonium compounds include, but are not limited to, tetramethylammonium hydroxide (TMAH); tetraethylammonium hydroxide; tetrabutylammonium hydroxide; trimethylbenzylammonium hydroxide and mixtures thereof. Examples of suitable quaternary phosphonium compounds include, but are not limited to, tetramethylphosphonium hydroxide; tetraethylphosphonium hydroxide; tetrabutylphosphonium hydroxide and mixtures thereof.

Preferred catalysts include tetramethylammonium hydroxide, sodium hydroxide and mixtures thereof. The product polycarbonate typically has a weight average molecular weight of about 5,000 to about 100,000, more preferably of about 10,000 to about 65,000, and most preferably about 18,000 to about 36,000 as measured by gel permeation chromatography versus polystyrene standards.

The reaction conditions of the melt polymerization are not particularly limited and may be conducted in a wide range of operating conditions. The reaction temperature is typically in the range of about 100 to about 350° C., more preferably about 180 to about 310° C. The pressure may be at atmospheric, or at an added pressure of from atmospheric to about 15 torr in the initial stages of the reaction, and at a reduced pressure at later stages, for example in the range of about 0.2 to about 15 torr. The reaction time is generally about 0.1 hours to about 10 hours.

The melt polymerization may be accomplished in one or more stages, as is known in the art. In one embodiment, the process is conducted as a two stage process. In the two stage process, the first stage is an oligomerization stage, and the second stage is a polymerization stage. In the first stage of this embodiment, the base, is introduced into the reaction system comprising the dihydroxy compound and the carbonic acid diester and the diarylester. The first stage is conducted at a temperature of 290° C. or lower, preferably 150 to 290° C., more preferably 200 to 280° C. The duration of the first stage is preferably 0 to 5 hours, even more preferably 0 to 3 hours at a pressure from atmospheric pressure to 100 torr, with a nitrogen atmosphere preferred. Alternatively, the base may be introduced prior to the first stage, in a monomer mix tank, for instance. The contents from the monomer mix tank are fed to the first stage, or anywhere in between. The molecular weight of the oligomer is less than 8,000 Mn.

The base catalyst is typically present in a range between about $10^{-8}$ moles and about $10^{-3}$ moles to moles of aromatic dihydroxy compound. In another embodiment, the catalyst is present in a range between about $10^{-7}$ moles and about $10^{-5}$ moles to moles of aromatic dihydroxy compound.

Additives may also be added to the polycarbonate product as long as they do not adversely affect the properties of the product. These additives include a wide range of substances that are conventionally added to the polycarbonates for a variety of purposes. Specific examples include heat stabilizers, epoxy compounds, ultraviolet absorbers, mold release agents, colorants, antistatic agents, slipping agents, anti-blocking agents, lubricants, antifogging agents, natural oils, synthetic oils, waxes, organic fillers, flame retardants, inorganic fillers and any other commonly known class of additives.

The reaction can be conducted as a batch or a continuous process. Any desired apparatus can be used for the reaction. The material and the structure of the reactor used in the present invention is not particularly limited as long as the reactor has an ordinary capability of stirring. It is preferable that the reactor is capable of stirring in high viscosity conditions as the viscosity of the reaction system is increased in later stages of the reaction.

EXAMPLES

The following examples are set forth to provide those of ordinary skill in the are with a complete description of how the compositions of matter and methods claimed herein are made and evaluated, and are not intended to limit the scope of what the inventors regard as their invention. Efforts have been made to insure accuracy with respect to numbers (e.g., amounts, temperature, etc.) but some errors and deviations should be accounted for. Unless indicated otherwise, parts are by weight, temperature is in degrees Celsius.

Molecular weights are reported as number average ($M_n$) and were determined by GPC analysis of polycarbonate prepared by melt polymerization. Standards of polystyrene were used to construct a universal calibration against which polycarbonate could be measured using the Mark-Houwink equation. The temperature of the columns was 25° C. and the mobile phase was chloroform.

The following is a description of how the preparation was prepared for sample 1 in Table. The remaining samples were prepared by an otherwise identical procedure using the other catalysts listed in Table 1, except as noted.

Synthesis of Sample 1

The following reactions were carried out in a 1 liter glass batch reactor equipped with a solid nickel helical agitator. The glass reactor surface was passivated by acid washing, rinsing, and subsequently drying overnight at 70° C. and stored covered until use.

The temperature of the reactor was maintained using a fluidized sand bath with a PID controller and measured near the reactor and sand bath interface. The pressure of the reactor was controlled by a nitrogen bleed into the vacuum pump downstream of the distillate collection flasks and measured at higher pressures (760 mm Hg to 40 mm Hg) with a mercury barometer, and at lower pressures (40 mm Hg to 1 mm Hg) with an Edward pirani gauge.

The reactor was charged with 0.6570 mol BPA and 0.7096 mol diphenyl carbonate prior to assembly. If the run was spiked with p-toluene sulfonic acid the acid was added as a solution with the NaOH or with the solution of TBPH at a later time during the reaction. The reactor was then assembled, sealed and the atmosphere was exchanged with nitrogen three times. With the final nitrogen exchange, the reactor was brought to about atmospheric pressure and submerged into the fluidized bath which was at 180° C. After five minutes, agitation was begun at 250 rpm. After an additional ten minutes, the reactants were fully melted and a homogeneous mixture was assumed. Tetramethyl ammonium hydroxide (TMAH, $1.32 \times 10^{-4}$ mol) and sodium hydroxide (NaOH, $5.00 \times 10^{-7}$ mol) were added sequentially after being diluted to the proper concentrations (0.220 M TMAH and $5.00 \times 10^{-3}$ M NaOH) with 18 Mohm water. The TBPH was added as an aqueous solution at this time, if appropriate. After the final catalyst was added, timing began, and the temperature was ramped to 210° C. in five minutes. Once at temperature, the pressure was reduced to 180 mm Hg and phenol distillate was immediately formed. After 25 minutes, the pressure was again reduced to 100 mm Hg and maintained for 45 minutes.

The temperature was then ramped to 240° C. in five minutes and the pressure was lowered to 15 mm Hg. These conditions were maintained for 45 minutes. The temperature was then ramped to 270° C. in five minutes and the pressure was lowered to 2 mm Hg. These conditions were maintained for 10 minutes. The temperature was then ramped to the final finishing temperature in five minutes and the pressure was reduced to 1.1 mm Hg. The finishing temperature was 310° C. After 30 minutes, the reactor was removed from the sand bath and the melt was extruded into liquid nitrogen to quench the reaction.

The results in Table 1 clearly illustrate the effectiveness of the addition of TBPH. Addition of a thermally stable organic base as described herein provides adequate neutralization of the acidic IER resin so as to slow down BPA cracking and not effect the subsequent melt polymerization in a negative manner. For example, addition of TBPH provides a negligible amount of branching side products produced by alkali metal bases, such as NaOH, yet is strong enough so as to effectively neutralize the residual sulfonic acid species, such as aryl sulfonic acid species, throughout the course of the polymerization. In the present examples, the addition of p-toluenesulfonic acid (pTSA) is used as a model for the sulfonated polystyrene IER. The effectiveness of the pTSA neutralization during polymerization was determined by the final molecular weight of the polymer. As can be seen from Table 1, Example 3, addition of an amount of pTSA to a polymerization, equivalent to the added sodium hydroxide, results in neutralization of the sodium hydroxide. Since the TMAH has relatively low thermal stability, it degrades very quickly during the polymerization leaving only the pTSA and NaOH which becomes effectively neutralized. In contrast, addition of TBPH results in complete elimination of the effects of added pTSA. The TBPH is more thermally stable than TMAH, and the enhanced thermal stability of the subsequent tetrabutyl phosphonium salt can also be inferred as the addition of even a factor of 10 lower concentration of TBPH vs TMAH in the presence of pTSA (see Example 8) provides the same molecular weight as the TMAH/NaOH polymerization (see Example 1).

Addition of pTSA to a standard polymerization with TMAH and NaOH results in very effective neutralization of the NaOH catalyst even though the TMAH is present in 250 times molar excess of the pTSA. In a spiking experiment substituting TBPH for TMAH, the effect of the pTSA was completely eliminated. The TBPH functioned as a very effective catalyst. The results of the spiking experiments further demonstrate the effectiveness of adding much lower levels of TBPH to the polymerization. In experiments conducted under standard conditions for the melt process (TMAH at $2.5 \times 10^{-4}$ and NaOH at $1.0 \times 10^{-6}$) pTSA was spiked at $1.0 \times 10^{-6}$ and incremental levels of TBPH were added. Significant impact for even low levels of TBPH were demonstrated as shown in Table 1 below. For example, at addition of only 10% of the TMAH loading of TBPH ($2.5 \times 10^{-5}$), molecular weight build equivalent to standard conditions without spiking pTSA is demonstrated.

TABLE 1

| Example | Catalyst | Co-Catalyst | PTSA | Mn |
|---|---|---|---|---|
| Controls | | | | |
| 1 | NaOH ($1.0 * 10^{-6}$) | TMAH ($2.5 * 10^{-4}$) | None | 8,552 |
| 2 | None | TMAH ($2.5 * 10^{-4}$) | None | 1440 |
| Spiking | | | | |
| 3 | NaOH ($1.0 * 10^{-6}$) | TMAH ($2.5 * 10^{-4}$) | $1.0 * 10^{-6}$ | 2545 |
| 4 | NaOH ($1.0 * 10^{-6}$) | TBPH ($2.5 * 10^{-4}$) | $1.0 * 10^{-6}$ | 10,066 |
| Adding TMAH at $2.5 * 10^{-4}$ | | | | |
| 5 | NaOH ($1.0 * 10^{-6}$) | TBPH ($4.0 * 10^{-6}$) | $1.0 * 10^{-6}$ | 2309 |
| 6 | NaOH ($1.0 * 10^{-6}$) | TBPH ($8.0 * 10^{-6}$) | $1.0 * 10^{-6}$ | 4423 |
| 7 | NaOH ($1.0 * 10^{-6}$) | TBPH ($1.6 * 10^{-5}$) | $1.0 * 10^{-6}$ | 6616 |
| 8 | NaOH ($1.0 * 10^{-6}$) | TBPH ($2.5 * 10^{-5}$) | $1.0 * 10^{-6}$ | 8470 |

As shown in the Table above, adding sufficient TBPH appears not to enhance the polymerization, but does effective neutralize the added pTSA as shown in a comparison of examples 1, 3 and example 8. The aryl sulfonic acid is essentially a polystyrene bound version of PTSA.

Additionally, an experiment was conducted to show cracking. Conditions: 100 grams BPA with 1.0 ppm pTSA heated at 225° C. for 2.5 hours.

| Added Base | % IPP (Isopropenyl phenol formed) |
|---|---|
| none | 0.11% |
| TBPA (1.0 molar equivalent) | 0.015 |
| NaOH | 0.015 |

BPA in the presence of acid (in this case PTSA) will begin to crack and form IPP (isopropenyl phenol). Therefore the more IPP that forms the more BPA is cracking. Conversely the less BPA the less cracking. Therefore, as shown above, the examples show both TBPA and NaOH inhibit the BPA cracking by neutralizing the PTSA present. With respect to the plant there is potential for minor acid contamination into the crude BPA stream by oligomeric Ion Exchange resin (IER, which is polymeric form of PTSA) fused to catalyze the BPA formation (from phenol and acetone). During the purification of BPA the remaining phenol is removed from the BPA by heat and vacuum (~180° C). At this temperature the presence of acid will begin to crack BPA. NaOH is added which effectively prevents cracking of the BPA by neutralizing pTSA. The problem is now the NaOH will end up in the melt polymerization and potentially cause Fries formation. Using the TBPA effectively neutralizes (and is thermally stable enough) the pTSA and does not cause Fries formation.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A method of preparing polycarbonate by the melt process, comprising:
   combining a thermally stable organic base with a crude dihydric phenol in the presence of a sulfonic acid compound and in the absence of an alkali metal compound or an alkaline earth metal compound to form a dihydric phenol;
   melting the dihydric phenol and a diester of carbonic acid for a time and at a temperature sufficient to form a melt product;
   combining the melt product with a catalyst comprising the alkali metal compound, the alkaline earth metal compound, a quaternary ammonium compound, a quaternary phosphonium compound, or a combination thereof;
   oligomerizing the melt product; and
   polymerizing the melt product.

2. The method of claim 1, wherein the thermally stable organic base is selected from the group consisting of tetraalkyl phosphonium hydroxides, tetraorganophosphonium carboxylic acid salts, and mixtures thereof.

3. The method of claim 1, wherein the dihydric phenol is 2,2-bis(4-hydroxy-phenyl)propane.

4. The method of claim 1, wherein the diester of carbonic acid is selected from the group consisting of diaryl carbonate, bis(4-t-butylphenyl) carbonate, bis (2,4-dichlorophenyl) carbonate, bis(2,4,6-trichlorphenyl) carbonate, bis(2-cyanophenyl) carbonate, bis(o-nitrophenyl) carbonate, ditolyl carbonate, m-cresol carbonate, dinaphthyl carbonate, bis(diaryl) carbonate, diethyl carbonate, dimethyl carbonate, dibutyl carbonate, dicyclohexyl carbonate, and mixtures thereof.

5. The method of claim 1, wherein polymerizing comprises polymerizing the melt product to a number average molecular weight of about 10,000 to about 65,000.

6. The method of claim 5, wherein the number average molecular weight is about 18,000 to about 36,000.

7. The method of claim 1, wherein the alkali metal compound is selected from the group consisting of sodium hydroxide, potassium hydroxide, lithium hydroxide, sodium hydrogen carbonate, potassium hydrogen carbonate, lithium hydrogen carbonate, sodium carbonate, potassium carbonate, lithium carbonate, sodium acetate, potassium acetate, lithium acetate, sodium stearate, potassium stearate, lithium stearate, sodium borohydride, lithium borohydride, sodium borophenolate, sodium benzoate, potassium benzoate, lithium benzoate, disodium hydrogen phosphate, dipotassium hydrogen phosphate, dilithium hydrogen phosphate, disodium salts of 2,2-bis(4-hydroxy-phenyl)propane, dipotassium salts of 2,2-bis(4-hydroxy-phenyl)propane, dilithium salts of 2,2-bis(4-hydroxy-phenyl)propane, sodium salts of phenol, potassium salts of phenol, and lithium salts of phenol, and the alkaline earth metal compound is selected from the group consisting of calcium hydroxide, barium hydroxide, magnesium hydroxide, strontium hydroxide, calcium hydrogen carbonate, barium hydrogen carbonate, magnesium hydrogen carbonate, strontium hydrogen carbonate, calcium carbonate, barium carbonate, magnesium carbonate, strontium carbonate, calcium acetate, barium acetate, magnesium acetate, strontium acetate, calcium stearate, barium stearate, magnesium stearate, and strontium stearate.

8. The method of claim 1, wherein the quaternary ammonium compound is selected from the group consisting of tetramethylammonium hydroxide, tetraethylammonium hydroxide, tetrabutylammonium hydroxide, trimethylbenzylammonium hydroxide, and mixtures thereof.

9. The method of claim 1, wherein the quaternary phosphonium compound is selected from the group consisting of tetramethylphosphonium hydroxide, tetraethylphosphonium hydroxide, tetrabutylphosphonium hydroxide, and mixtures thereof.

10. The method of claim 1, wherein combining the thermally stable organic base with the crude dihydric phenol in the presence of the sulfonic acid compound comprises combining an amount of the thermally stable organic base sufficient to neutralize the sulfonic acid compound.

11. The method of claim 10, wherein the thermally stable organic base is present in an amount of about 1 to about 25 molar equivalents per mole of the sulfonic acid compound.

12. The method of claim 1, further comprising combining the melt product with about 0.01 to about 0.20 moles per mole of the dihydric phenol of an endcapping agent selected from the group consisting of monovalent aromatic hydroxy compounds, haloformate derivatives of monovalent aromatic hydroxy compounds, monovalent carboxylic acids, halide derivatives of monovalent carboxylic acids, and mixtures thereof.

13. The method of claim 1, wherein the catalyst is present in an amount of about $10^{-8}$ to about $10^{-3}$ moles per mole of the dihydric phenol.

14. The method of claim 1, wherein melting is at about 180 to about 310° C. for about 0.1 to about 10 hours.

15. A method of preparing polycarbonate by the melt process, comprising:

combining a thermally stable organic base selected from the group consisting of tetraalkyl phosphonium hydroxides, tetraorganophosphonium carboxylic acid salts, and mixtures thereof, with a crude dihydric phenol in the presence of a sulfonic acid compound and in the absence of an alkali metal compound or an alkaline earth metal compound to form a dihydric phenol, wherein the thermally stable organic base is present in an amount sufficient to neutralize the sulfonic acid compound;

melting the dihydric phenol and a diester of carbonic acid for a time and at a temperature sufficient to form a melt product;

combining the melt product with a catalyst comprising the alkali metal compound, the alkaline earth metal compound, a quaternary ammonium compound, a quaternary phosphonium compound, or a combination thereof;

oligomerizing the melt product; and polymerizing the melt product.

16. The method of claim 15, wherein the dihydric phenol is 2,2-bis(4-hydroxy-phenyl)propane, and the diester of carbonic acid is diphenyl carbonate.

17. The method of claim 15, wherein the quaternary ammonium compound is selected from the group consisting of tetramethylammonium hydroxide, tetraethylammonium hydroxide, tetrabutylammonium hydroxide, trimethylbenzylammonium hydroxide, and mixtures thereof, and the quaternary phosphonium compound is selected from the group consisting of tetramethylphosphonium hydroxide, tetraethylphosphonium hydroxide, tetrabutylphosphonium hydroxide, and mixtures thereof.

18. The method of claim 15, wherein the catalyst is present in an amount of about $10^{-8}$ to about $10^{-3}$ moles per mole of the dihydric phenol.

19. The method of claim 15, wherein melting is at about 180 to about 310° C. for about 0.1 to about 10 hours.

* * * * *